United States Patent
Yoon et al.

(10) Patent No.: US 7,189,241 B2
(45) Date of Patent: Mar. 13, 2007

(54) APPARATUS FOR PREPARING FEMORAL CAVITY USING VIBRATION UNDER OPERATION OF FIXING GUIDE UNIT

(75) Inventors: Yong San Yoon, Daejeon (KR); Young Bae Park, Cheongju-si (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 10/985,297

(22) Filed: Nov. 10, 2004

(65) Prior Publication Data

US 2005/0113839 A1 May 26, 2005

(30) Foreign Application Priority Data

Nov. 26, 2003 (KR) .................. 10-2003-0084338

(51) Int. Cl.
*A61B 17/00* (2006.01)
(52) U.S. Cl. ..................................................... 606/85
(58) Field of Classification Search ............. 606/79, 606/80, 82, 84, 87, 99; 623/23.11–23.38
See application file for complete search history.

(56) References Cited

U.S. PATENT DOCUMENTS 5,057,112 A * 10/1991 Sherman et al. ............. 606/79

5,152,352 A 10/1992 Mandanis
2003/0171756 A1 * 9/2003 Fallin et al. .................. 606/80
2005/0192583 A1 * 9/2005 Walker et al. ................ 606/79

\* cited by examiner

*Primary Examiner*—Pedro Philogene
*Assistant Examiner*—Michael J. Araj
(74) *Attorney, Agent, or Firm*—Thomas R. FitzGerald, Esq.; Hiscock & Barclay, LLP

(57) ABSTRACT

Disclosed herein is a femoral broaching apparatus for use in preparing a femoral cavity for implantation of a prosthetic joint in surgical orthopedic artificial hip joint replacement arthroplasty procedures. The apparatus comprises a fixing guide unit fixed in the femoral cavity by an interference fit, a cavity preparing broach coupled to the fixing guide unit in a longitudinally movable manner, and a vibration-generating unit coupled to the cavity preparing broach for allowing the cavity preparing broach to perform the preparing of the femoral cavity under operation of the fixing guide unit. According to the present invention, a femoral cavity having an intended accurate shape can be easily prepared using mechanical vibration rather than a manual operation, thereby ensuring operational convenience. Further, since the preparing of the femoral cavity is performed under axial guiding operation of a fixing guide unit, the shape accuracy of the resulting femoral cavity as well as the positional accuracy of a tool, such as a surgical broach, can be improved.

6 Claims, 5 Drawing Sheets

APPARATUS FOR PREPARING FEMORAL CAVITY USING VIBRATION UNDER OPERATION OF FIXING GUIDE UNIT

CROSS-REFERENCE TO RELATED APPLICATIONS

This application claims the benefit of the filing date of Korean Patent Application Number 10-2003-0084338, filed Nov. 26, 2003.

BACKGROUND OF THE INVENTION

1. Field of the Invention

The present invention relates to a femoral broaching apparatus for use in preparing a femoral cavity for implantation of a prosthetic joint in the case of a surgical artificial hip-joint replacement arthroplasty, and more particularly, to a femoral broaching apparatus which can prepare a femoral cavity having accurate shape and position using vibration under operation of a fixing guide unit.

2. Background of the Related Art

Artificial hip joint replacement arthroplasty involves the fixation of a prosthetic hip joint to a proximal end of the femur. For this, the damaged femoral head is first removed, and then the prosthetic hip joint is inserted into the femur so as to come into smooth contact with the pelvis without pain. Here, the prosthetic hip joint serves as a joint prosthesis for connecting the femur to the pelvis. For the secure and durable fixation of the femoral prosthesis, its design has been evolved during past decades. Currently, except very unusual case, the femoral prosthesis is designed to fill the proximal femur. Proximal femoral spongeous bone is shaped as the prosthesis during the surgery by drill or broach. Then the prosthesis inserted into the femoral cavity which prepared. Machined cavity should be aligned and connected with the original femoral cavity. Otherwise the femoral prosthesis fails to obtain proper fixation.

After the completion of implantation, the joint prosthesis is securely fixed relative to the femur and is adapted to transmit the weight of a patient to the femur. Examples of methods for fixing the joint prosthesis to the femur include an adhesive method using a bone cement, and a non-adhesive method using ingrowth of new tissue of the femur into the joint prosthesis for achieving mechanical interlocking therebetween. Although one of the fixing methods can be appropriately selected and used according to the patient's condition, specifically, in the case of the non-adhesive method, it is known that the shape accuracy of the femoral cavity largely affects the results of the surgical operation.

In addition to the shape accuracy thereof, the positional accuracy of the femoral cavity is also important. If the femoral cavity is not at an intended accurate position, it may result in distortion or shortening of the patient's leg after the completion of the prosthetic hip replacement.

In the prior art, for the preparing of the femoral cavity, a surgical broach is manually inserted into the femur through hammering. Here, the surgical broach has the same shape as that of the prosthetic joint to be implanted in the femur. This method, however, has a problem of inaccuracy in shape and position of the resulting femoral cavity. Instead of such a manual hammering method, further, a high-speed pneumatic vibrator is used to insert the broach into the femur. This has been proved to enhance operational convenience as compared to the manual hammering operation, but it still suffers from poor reliability in the accuracy of shape and position of the resulting femoral cavity.

As yet another method, a computerized robotic milling system is used for the preparing of the femoral cavity. In the case of this robotic system, although it can successfully prepare the femoral cavity having desired accurate shape and position, it has the problems of its costly price and relatively long operational time. In some cases, furthermore, there exists the necessity of additional surgical procedures, resulting in enormous cost load as well as the risk of thrombosis due to excessive bleeding of the patient.

SUMMARY OF THE INVENTION

Accordingly, the present invention has been made in view of the above problems, and it is an object of the present invention to provide a femoral broaching apparatus in which a broach is inserted into the femur by means of a high-speed electric or pneumatic vibration-generating unit under operation of a fixing guide unit, so as to allow the broach to accurately cut a femoral cavity to have a desired position and direction, thereby resulting in a remarkable improvement in the accuracy of the shape and position of the resulting femoral cavity.

In the present invention, specifically, the guide unit can be easily and rapidly aligned with the femur and positioned optimally relative to the femur since it is mounted in the intramedullary femoral cavity. This allows the resulting femoral cavity to be accurately positioned relative to the femur. Specifically, mounting the guide unit inside the femoral cavity can increase accuracy in selection and alignment of desired positions of the femoral cavity.

After completing the mounting of the guide unit as stated above, according to the present invention, a clinically important valgus-varus angle can be simply tuned by means of a screw.

Accordingly, it is yet another object of the present invention to provide a femoral broaching apparatus which can improve accuracy in the shape and position of a femoral cavity through appropriate position tuning of a surgical broach used in preparing the femur, and can allow easy preparing of the femoral cavity using mechanical vibration rather than manual operation, eliminating operational inconvenience during broaching.

To achieve the above object, according to an aspect of the present invention, there is provided a femoral broaching apparatus for preparing a femoral cavity using vibration under operation of a fixing guide unit for the implantation of a prosthetic joint into the femur, including: a fixing guide unit fixed in the femoral cavity by an interference fit; a cavity preparing broach coupled to the fixing guide unit in a longitudinally movable manner; and a vibration-generating unit coupled to the cavity preparing broach for allowing the cavity preparing broach to perform the preparing of the femoral cavity under operation of the fixing guide unit.

Preferably, the fixing guide unit may include: a fixing portion formed at one end thereof, the fixing portion being fixedly fitted in the femoral cavity; and a guiding shaft formed at the other end thereof, the guiding shaft being adapted to guide the cavity preparing broach so as to move only in a vertical direction.

Preferably, the cavity preparing broach may include cutting teeth formed at the overall peripheral surface thereof for cutting the femoral cavity suitable to accommodate the prosthetic joint.

Preferably, the vibration-generating unit may include: a vibrating body connected to the cavity preparing broach; a driving motor fixedly mounted in the vibrating body; and a vibrating plate rotatably installed in the vibrating body, the vibrating plate being adapted to rotate upon receiving a rotating force from the driving motor, and to repeatedly displace a rotational center thereof, causing vibration of the vibrating body.

Preferably, the vibrating plate may have a disk form, and may be provided at a position along the periphery thereof with a weight, the weight serving to induce vibrations.

Preferably, the vibration-generating unit may include: a piston housing connected to the cavity preparing broach; a piston mounted in the piston housing in a vertically movable manner; a switching member for repeating vertical movements of the piston; and a pneumatic source connected to the switching member and adapted to apply a pneumatic pressure to a pneumatic chamber of the piston.

Preferably, the apparatus may further comprise a direction tuning unit serving as means for setting the advance direction of the cavity preparing broach.

Preferably, the direction tuning unit may include: a rotation joint located between the fixing guide unit and the cavity preparing broach, the rotation joint being coupled to the fixing guide unit so as to simultaneously rotate together with the fixing guide unit, and is also assembled to the cavity preparing broach in a rotatable manner; and a locker mounted on the cavity preparing broach in order to adjust rotation of the rotation joint and to fix the rotation joint.

Preferably, the rotation joint may be formed with a pinion gear, and the locker may be formed with a worm gear adapted to engage with the pinion gear.

BRIEF DESCRIPTION OF THE DRAWINGS

Further objects and advantages of the invention can be more fully understood from the following detailed description taken in conjunction with the accompanying drawings in which.

DETAILED DESCRIPTION OF THE PREFERRED EMBODIMENT

Now, preferred embodiments of the present invention will be described in detail with reference to the annexed drawings. The following description has been made only for a better understanding of the present invention, and thus the scope and sprit of the present invention must not be limited to the following description and the accompanying drawings.

Figure 1:
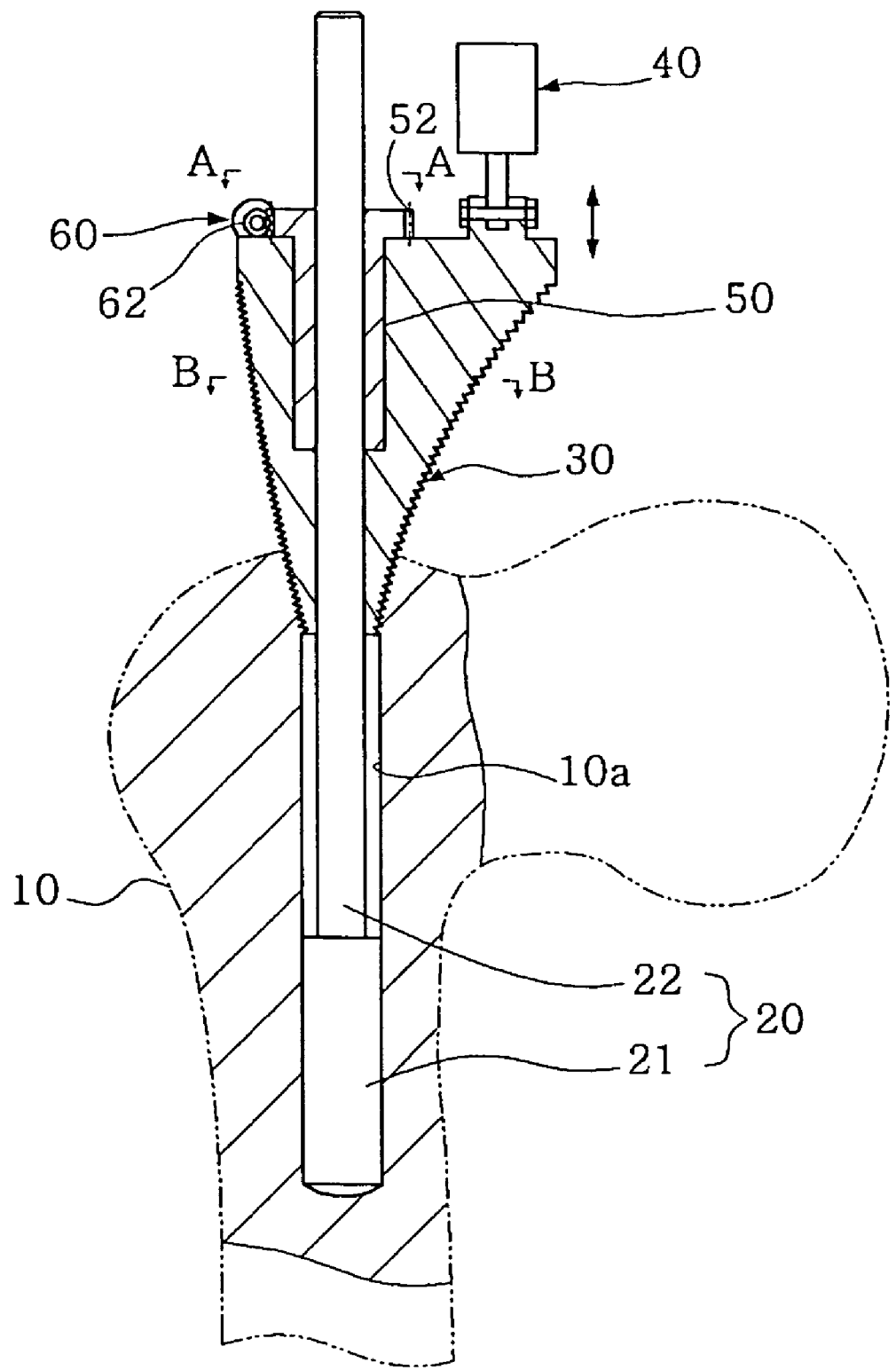
FIG. 1 is a sectional view illustrating an assembled state of a femoral broaching apparatus in accordance with the present invention.
Figure 2:
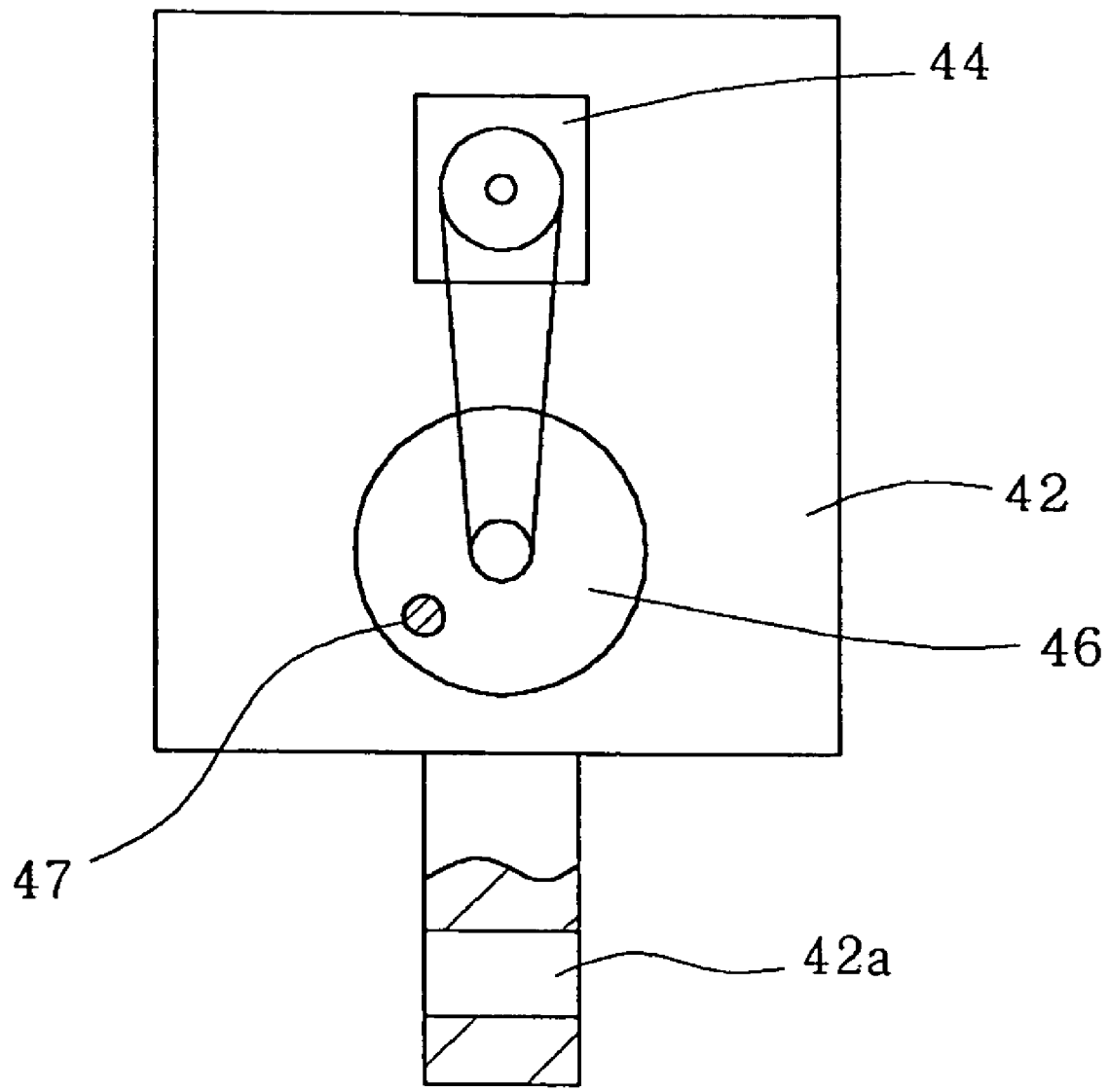
FIG. 2 is a diagrammatic view illustrating a vibration-generating unit in accordance with one embodiment of the present invention.
Figure 3:
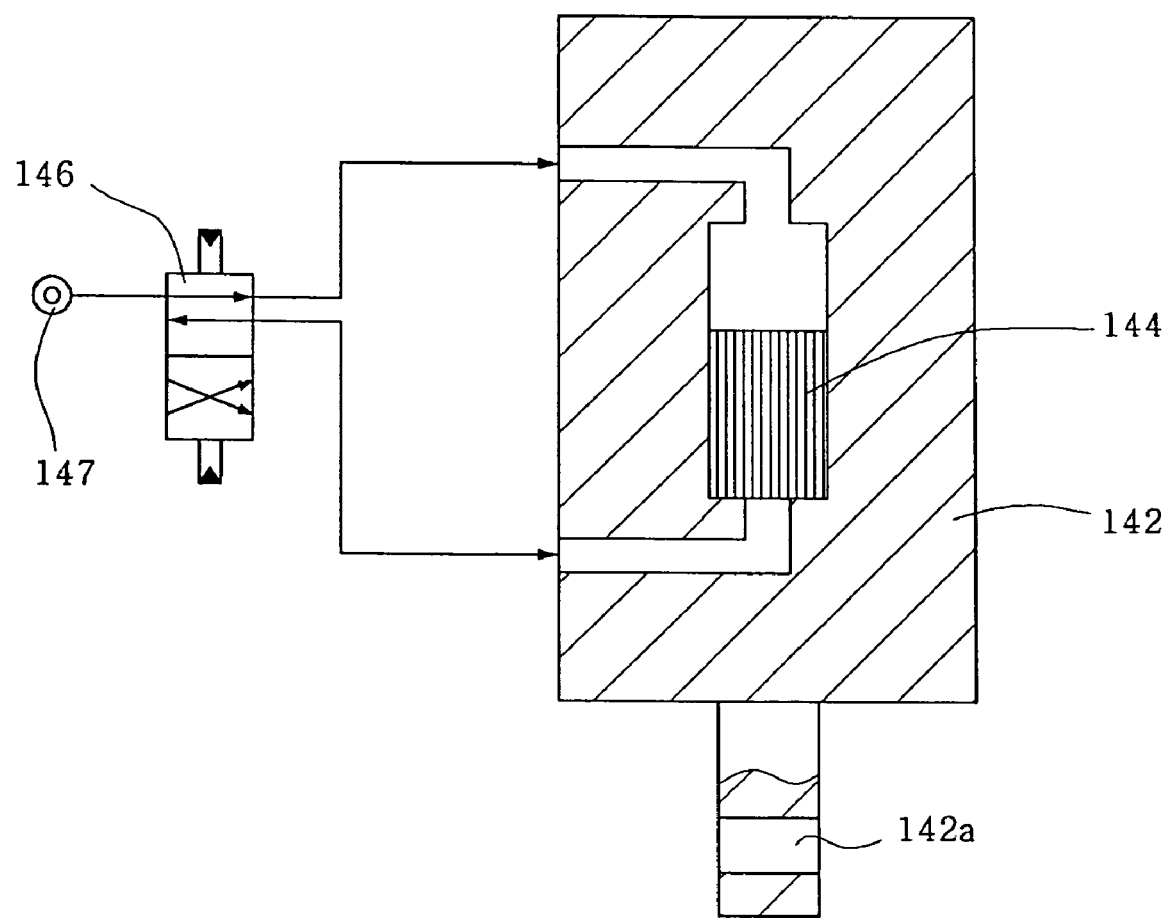
FIG. 3 is a diagrammatic view illustrating a vibration-generating unit in accordance with another embodiment of the present invention.
Figure 4:
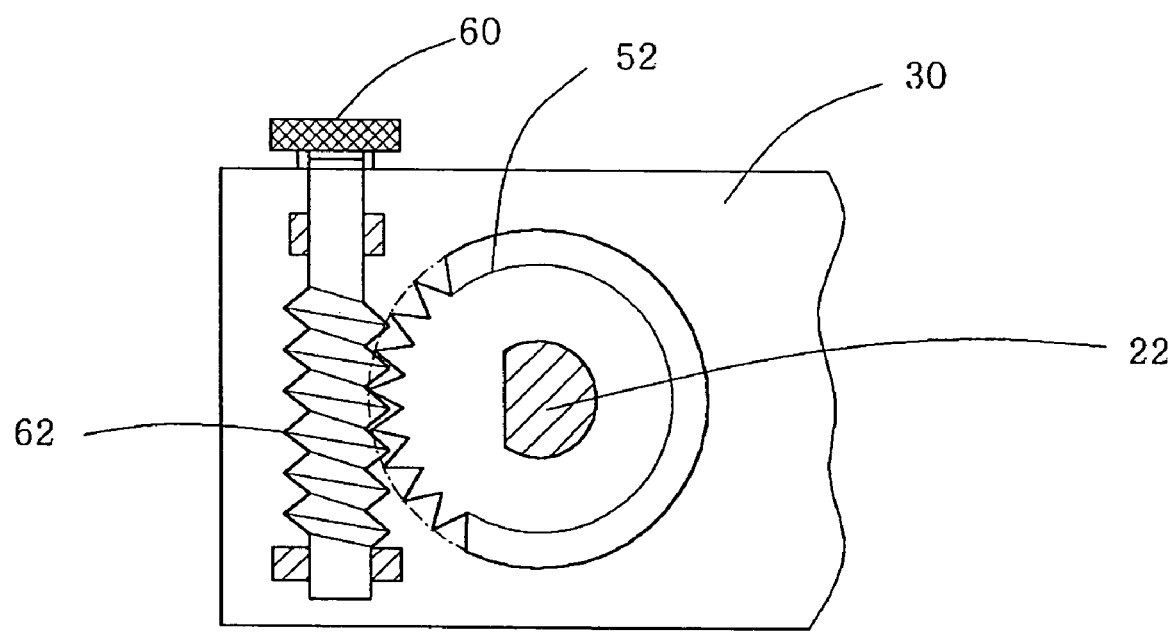
FIG. 4 is a cross sectional view taken along the line A—A shown in FIG. 1.
Figure 5:
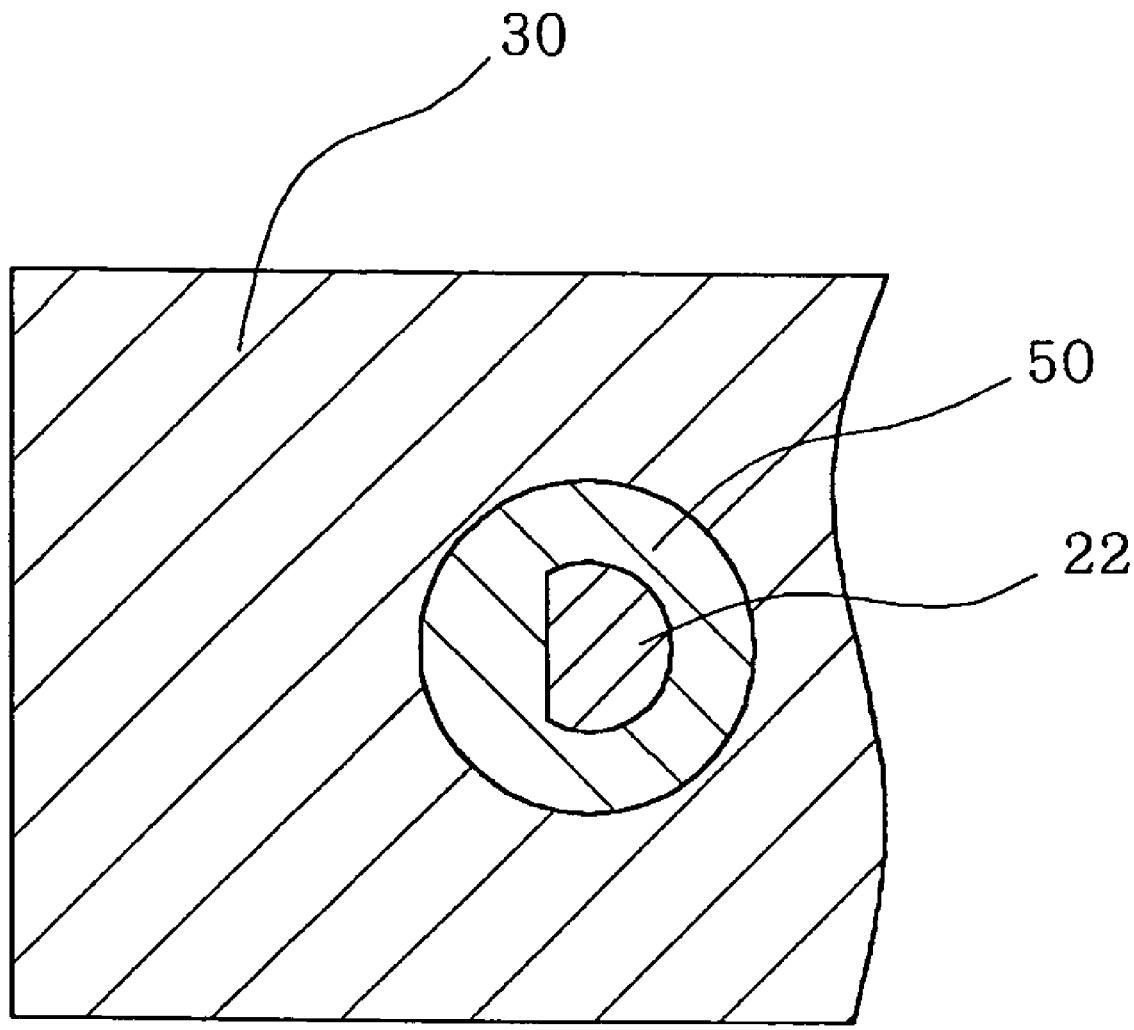
FIG. 5 is a cross sectional view taken along the line B—B shown in FIG. 1.

FIG. 1 is a sectional view illustrating an assembled state of a femoral broaching apparatus in accordance with the present invention. FIGS. 2 and 3 are diagrammatic views respectively illustrating different embodiments of a vibration-generating unit in accordance with the present invention. FIG. 4 is a cross sectional view taken along the line A—A shown in FIG. 1, and FIG. 5 is a cross sectional view taken along the line B—B shown in FIG. 1.

As shown in FIG. 1, the femoral broaching apparatus of the present invention comprises a fixing guide unit 20 for use in preparing an accurate femoral cavity 10a for implantation of a prosthesis device, such as a prosthetic hip joint (not shown), into a femur 10.

The fixing guide unit 20 is fixed to the femur 10 by an interference fit.

In the femoral broaching apparatus of the present invention, a plurality of fixing guide units 20, having different sizes, may be provided to be selectively used in various different sizes of the patient's femoral cavity. Such a fixing guide unit 20 serves to axially align the femoral cavity along a central longitudinal axis of the femur 10 during broaching. The fixing guide unit 20 includes a fixing portion 21 formed at one end thereof, and a guiding shaft 22 formed at the other end thereof. The fixing portion 21 is inserted into the femoral cavity and fixed therein by friction. The guiding shaft 22 serves to guide a surgical broach 30 to move only in a vertical direction for preparing the femoral cavity, as will be explained below.

The cavity preparing broach 30 is coupled to the fixing guide unit 20. More particularly, the cavity preparing broach 30 is installed in such a manner that it is vertically movable along a longitudinal direction of the guiding shaft 22 of the fixing guide unit 20.

Such a cavity preparing broach 30 is formed at the overall outer peripheral surface thereof with cutting teeth, and thus serves as a tool of cutting a desired femoral cavity having a size suitable to accommodate the prosthetic joint (not shown).

Onto the cavity preparing broach 30 is fixedly or detachably coupled a vibration-generating unit 40. The vibration-generating unit 40 serves to generate vibration sufficient to cause vertical movement of the cavity preparing broach 30 coupled to the fixing guide unit 20.

The vibration-generating unit 40 may be of electric type or pneumatic type.

Considering first an electric vibration-generating unit as shown in FIG. 2, the electric vibration-generating unit comprises a vibrating body 42 connected to the cavity preparing broach 30, a driving motor 44 fixedly mounted in the vibrating body 42, and a vibrating plate 46 rotatably installed in the vibrating body 42. The vibrating plate 46 is adapted to rotate upon receiving a rotating force from the driving motor 44. During rotation, a rotational center of the vibrating plate 46 is repeatedly displaced, causing vibration of the vibrating body 42.

In the present embodiment, the vibrating plate 46 has a disk form, and is provided at a position along the periphery thereof with a weight 47. The weight 47 is used to induce vibrations.

That is, when the driving motor 44 rotates, the weight 47 of the vibrating plate 46 acts to displace the rotational center of the vibrating plate 46, thereby causing the vibrating body 42, which is confined by the cavity preparing broach 30, to vertically vibrate.

Next, considering a pneumatic vibration-generating unit as shown in FIG. 3, the pneumatic vibration-generating unit comprises a piston housing 142 connected to the cavity preparing broach 30, a piston 144 mounted in the piston housing 142 in a vertically movable manner, a switching member 146 for repeating vertical movements of the piston 144, and a pneumatic source 147 connected to the switching member 146 and adapted to apply a pneumatic pressure to a pneumatic chamber of the piston 144. In this case, the switching member 146 is electrically controlled, so that it controls the movement direction of the piston 144 according to the change of its switching position.

The femoral broaching apparatus of the present invention further comprises a direction tuning unit, which serves as means for setting the advance direction of the cavity preparing broach 30. The direction tuning unit comprises a rotation joint 50 located between the fixing guide unit 20 and the cavity preparing broach 30, and a locker 60 mounted on the cavity preparing broach 30 in order to adjust rotation of the rotation joint 50 and to fix the rotation joint 50. Here, the rotation joint 50, on one hand, is coupled to the fixing guide unit 20 so as to simultaneously rotate together with the fixing guide unit 20, and on the other hand, is assembled to the cavity preparing broach 30 in a rotatable manner.

In this case, both the rotation joint 50 and the fixing guide unit 20 may have a half-moon shaped coupling cross section as shown in FIG. 5.

Here, as shown in FIG. 4, the rotation joint 50 is formed at an upper end thereof with a pinion gear 52, and correspondingly, the locker 60 is formed with a worm gear 62, so that the worm gear 62 and the pinion gear 52 are engaged with each other. That is, according to rotating direction of the locker 60, the worm gear 62 is engaged and rotated along the periphery of the pinion gear 52, thereby enabling tuning in a rotating degree of the cavity preparing broach 30 in a state wherein the locker 60 is fixed to the cavity preparing broach 30. In this case, the rotation joint 50 is fixedly maintained so as not to rotate since it is coupled to the fixing guide unit 20 while forming the above described half-moon shaped coupling cross section.

In the present embodiment, although the fixing guide unit 20 is shown and explained to have the half-moon shaped cross section, it will be clearly understood that the cross sectional shape of the fixing guide unit 20 is not limited thereto, and can be freely selected from among rectangular, square, triangular shapes, or the like so long as it can be fixedly coupled to the rotation joint 50 so as not to rotate.

Not explained reference numerals 42*a* and 142*a* refer to jointing holes for use in the connection of the cavity preparing broach 30.

Now, the operation of the present invention configured as stated above will be explained.

First, the femoral cavity of the femur 10 is axially enlarged by means of a reamer (not shown), so as to accommodate the fixing guide unit 20. In this case, the fixing portion 21 of the fixing guide unit 20 is securely kept in the femoral cavity using a frictional force caused by an interference fit.

Then, the cavity preparing broach 30 is coupled to the guide shaft 22 of the fixing guide unit 20.

In a coupled state, the advance direction of the cavity preparing broach 30 is inspected and tuned into a desired direction by means of the rotation joint 50 and the locker 60.

That is, in a state wherein the worm gear 62 of the locker 60 is engaged with the pinion gear 52 of the rotation joint 50, the locker 60 is rotated in a direction, causing the cavity preparing broach 30 to simultaneously rotate together with the locker 60.

In this way, through the operation of the locker 60, the advance direction of the cavity preparing broach 30 is determined, and successively, the vibration-generating unit 40 is operated to generate vibration.

The vibration generated upon operation of the vibration-generating unit is transmitted to the cavity preparing broach 30, allowing the cavity preparing broach 30 to repeatedly slightly move upward or downward.

Meanwhile, considering the generation of the vibration, first, in the case of the electric vibration-generating unit as shown in FIG. 2, the driving motor 44, connected to an electric source, is driven and correspondingly, the vibrating plate 46 is rotated, generating vibrations. Further, in the case of the pneumatic vibration-generating unit as shown in FIG. 3, the piston 144, connected to the pneumatic source 147, is repeatedly moved upward or downward, generating vibrations.

After that, as the cavity preparing broach 30 is repeatedly slightly moved in an axial vertical direction with a short time under operation of the fixing guide unit 20, the cavity preparing broach 30 is inserted into the femoral cavity to cut soft porous bone.

During broaching, an uppermost region of the fixing guide unit 20 is grasped by one hand, and the vibration-generating unit 40 is grasped by the other hand.

After femoral cavity preparing completion, both the cavity preparing broach 30 and the vibration-generating unit 40 are separated from the fixing guide unit 20, and finally, the fixing guide unit 20 is removed from the femur 10.

As stated above, the cavity preparing broach 30 prepares a desired shape of the femoral cavity while being guided along the fixing guide unit 20, resulting in an improved precision in preparing the femur. Further, by virtue of the above described mechanical operation rather than a manual operation, the preparing of the femoral cavity can be more easily and safely performed.

As apparent from the above description, the present invention provides a femoral broaching apparatus for use in surgical artificial hip joint replacement arthroplasty procedures. With the femoral broaching apparatus of the present invention, a femoral cavity having an intended accurate shape can be easily prepared using mechanical vibration rather than a manual operation, thereby ensuring operational convenience. Further, since the preparing of the femoral cavity is performed under axial guiding operation of a fixing guide unit, the shape accuracy of the resulting femoral cavity as well as the positional accuracy of a tool, such as a surgical broach, can be improved.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A femoral broaching apparatus for preparing a femoral cavity using vibration under operation of a fixing guide unit for implantation of a prosthetic joint to a femur, comprising:
    a fixing guide unit fixed in the femoral cavity by an interference fit;
    a cavity preparing broach coupled to the fixing guide unit in a longitudinally movable manner;
    a vibration-generating unit coupled to the cavity preparing broach for allowing the cavity preparing broach to perform the preparing of the femoral cavity under operation of the fixing guide unit; and
    wherein the vibration-generating unit includes:
        a vibrating body connected to the cavity preparing broach;
        a driving motor fixedly mounted in the vibrating body; and
        a vibrating plate rotatably installed in the vibrating body, the vibrating plate being adapted to rotate upon receiving a rotating force from the driving motor, and to repeatedly displace a rotational center thereof, causing vibration of the vibrating body.

2. The femoral broaching apparatus as claimed in claim 1, wherein the vibrating plate has a disk form, and is provided at a position along the periphery thereof with a weight, the weight serving to induce vibrations.

3. A femoral broaching apparatus for preparing a femoral cavity using vibration under operation of a fixing guide unit for implantation of a prosthetic joint to a femur, comprising:
- a fixing guide unit fixed in the femoral cavity by an interference fit;
- a cavity preparing broach coupled to the fixing guide unit in a longitudinally movable manner;
- a vibration-generating unit coupled to the cavity preparing broach for allowing the cavity preparing broach to perform the preparing of the femoral cavity under operation of the fixing guide unit; and wherein the vibration-generating unit includes:
- a piston housing connected to the cavity preparing broach;
- a piston mounted in the piston housing in a vertically movable manner;
- a switching member for repeating vertical movements of the piston; and
- a pneumatic source connected to the switching member and adapted to apply a pneumatic pressure to a pneumatic chamber of the piston.

4. A femoral broaching apparatus for preparing a femoral cavity using vibration under operation of a fixing guide unit for implantation of a prosthetic joint to a femur, comprising:
- a fixing guide unit fixed in the femoral cavity by an interference fit;
- a cavity preparing broach coupled to the fixing guide unit in a longitudinally movable manner;
- a vibration-generating unit coupled to the cavity preparing broach for allowing the cavity preparing broach to perform the preparing of the femoral cavity under operation of the fixing guide unit;
- a direction tuning unit serving as means for setting the advance direction of the cavity preparing broach; and wherein the direction tuning unit includes:
- a rotation joint located between the fixing guide unit and the cavity preparing broach, the rotation joint being coupled to the fixing guide unit so as to simultaneously rotate together with the fixing guide unit, and being also assembled to the cavity preparing broach in a rotatable manner; and
- a locker mounted on the cavity preparing broach in order to adjust rotation of the rotation joint and to fix the rotation joint.

5. The femoral broaching apparatus as claimed in claim 4, wherein the rotation joint is formed with a pinion gear, and the locker is formed with a worm gear adapted to engage with the pinion gear.

6. The femoral broaching apparatus as claimed in claim 4, wherein the rotation joint and the fixing guide unit have a half-moon shaped coupling cross section.

* * * * *